United States Patent
Klimko

(10) Patent No.: US 6,462,080 B1
(45) Date of Patent: Oct. 8, 2002

(54) PROSTAGLANDIN E RECEPTOR AGONISTS FOR TREATMENT OF DRY EYE

(75) Inventor: Peter G. Klimko, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/462,719

(22) PCT Filed: Dec. 14, 1999

(86) PCT No.: PCT/US99/29733

§ 371 (c)(1),
(2), (4) Date: Jan. 12, 2000

(87) PCT Pub. No.: WO00/38690

PCT Pub. Date: Jul. 6, 2000

Related U.S. Application Data

(60) Provisional application No. 60/113,574, filed on Dec. 24, 1998.

(51) Int. Cl.$^7$ .................. A61K 31/215; A61K 31/19
(52) U.S. Cl. .................. 514/530; 514/573; 514/912
(58) Field of Search .................. 514/530, 573, 514/912

(56) References Cited

U.S. PATENT DOCUMENTS

| | | |
|---|---|---|
| 3,991,759 A | 11/1976 | Urquhart |
| 4,131,651 A | 12/1978 | Shah et al. |
| 4,370,325 A | 1/1983 | Packman |
| 4,388,324 A | 6/1983 | Horrobin |
| 4,409,205 A | 10/1983 | Shively |
| 4,744,980 A | 5/1988 | Holly |
| 4,753,945 A | 6/1988 | Gilbard et al. |
| 4,818,537 A | 4/1989 | Guo |
| 4,868,154 A | 9/1989 | Gilbard et al. |
| 4,883,658 A | 11/1989 | Holly |
| 4,914,088 A | 4/1990 | Glonek et al. |
| 4,966,773 A | 10/1990 | Gressel et al. |
| 5,075,104 A | 12/1991 | Gressel et al. |
| 5,151,444 A | 9/1992 | Ueno et al. |
| 5,290,572 A | 3/1994 | MacKeen |
| 5,294,607 A | 3/1994 | Glonek et al. |
| 5,403,841 A | 4/1995 | Lang |
| 5,455,265 A | 10/1995 | Chandraratna |
| 5,620,921 A | 4/1997 | Sullivan |
| 5,658,948 A | 8/1997 | Lucero |
| 5,696,166 A | 12/1997 | Yanni et al. |

OTHER PUBLICATIONS

Bunce et. al., GR63799X—a novel prostanoid with selectivity for EP$_3$ receptors, *Adv. Prostaglandin, Thromboxane, Leukotriene Res.*, 21A:379–82 (1990).

Coleman et al., "VIII. International Union of Pharmacology classification of prostanoid receptors: Properties, distribution, and structure of the receptors and their subtypes," *Pharmacological Reviews*, 46(2):205–229 (1994).

Dartt et al., "Vasoactive intestinal peptide–stimulated glycocongjugate secretion from conjuctival goblet cells," *Exp. Eye Res.*, 63:27–34 (1996).

Dilly et al., "Surface Changes in the Anaesthetic Conjunctiva in Man, with Special Reference to the Production of Mucus from a Non–Goblet–Cell Source," *British Journal of Ophthalmology*, 65:833–842 (1981).

Enss et al., "Effects of PGE$_2$ and of different synthetic PGE derivatives on the glycosylation of pig gastric mucins," *Prostaglandins, Leukotrienes, Essent. Fatty Acids*, 59(1):49–54 (1998).

Gilbard, "Dry eye: pharmacological approaches, effects, and progress," *The CLAO Journal*, 22(2):141–145 (1996).

Gipson and Inatomi, "Mucin genes expressed by ocular surface epithelium," *Progress in Retinal and Eye Research*, 16(1):81–98 (1997).

Greiner et al., "Mucus Secretory Vesicles in Conjunctival Epithelial Cells of Wearers of Contact Lenses," *Archives of Ophthalmology*, 98:1843–1846 (1980).

Guslandi et. al., "Gastric effects of a prostaglandin E$_1$–derivative (Rioprostil) on acid,. alkaline, and mucus secretion," *Clin. Ther.*, 8(6):619–23 (1986).

Katz et. al., "Antigastrolesive, gastric antisecretory, diarrheagenic and mucus–stimulating effects in rats following topically applied rioprostil, a synthetic prostaglandin E$_1$ analog," *Life Sci.*, 41(12):1591–8 (1987).

Lemp, "Report of the National Eye Institute/Industry Workshop on Clinical Trials in Dry Eyes," *The CLAO Journal*, 21(4):221–231 (1995).

Nakamura et al., "Gefarnate stimulates secretion of mucin–like glycoproteins by corneal epithelium in vitro and protects corneal epithelium from dessication in vivo," *Experimental Eye Research*, 65:569–574 (1997).

Perkins et. al., "Antisecretory, mucosal–protective, and diarrheagenic activity of a novel synthetic prostaglandin, SC–46275, in the rat," *Drug Dev. Res.*, 23:349–58 (1991).

Schein et al., "Prevalence of dry eye among the elderly," *American J. Ophthalmology*, 124(6):723–728 (1997).

Sellers et. al., "Misoprostol–induced increases in adherent gastric mucus thickness and luminal mucus output," *Dig. Dis. Sci.*, 31(2):91S–95S (1986).

Watanabe et al., "Human Corneal and Conjuctival Epithelia Produce a Mucin–Like Glycoprotein for the Apical Surface," *Investigative Ophthalmology and Visual Science (IOVS)*, 36(2):337–344 (1995).

(List continued on next page.)

Primary Examiner—Zohreh Fay
(74) Attorney, Agent, or Firm—Barry L. Copeland

(57) ABSTRACT

The present invention relates to use of prostaglandin E receptor agonists and partial agonists to stimulate mucin secretion to treat dry eye, keratoconjunctivitis, Sjogren's syndrome and related ocular surface diseases.

8 Claims, No Drawings

OTHER PUBLICATIONS

Waterbury et. al., "Stimulatory effect of emprostil, an anti-ulcer prostaglandin, on gastric mucus secretion," *Am. J. Med.,* 81(2A):30–3 (1986).

Waterbury et. al., "Stimulation of mucus production and prevention of aspirin induced ulcerogenesis by enprostil in the rat," *Proc. West. Pharmacol. Soc.,* 31:21–3 (1988).

Wilson et. al., "Effects of misoprostol on gastric acid and mucus secretion in man," *Dig. Dis. Sci.,* 31(2):126S–129S (1986).

Yanni et al, "Effect of Intravenously Administered Lipoxygenase Metabolites on Rat Tracheal Mucous Gel Layer Thickness," *International Archives of Allergy And Applied Immunology,* 90:307–309 (1989).

Horrobin, "Essential fatty acid metabolism in diseases of connective tissue with special reference to scleroderma and to Sjogren's syndrome" Med. Hypotheses 14(3):233–47 (1984), Database Accession No. 101:128381 XP002143256 abstract.

PROSTAGLANDIN E RECEPTOR AGONISTS FOR TREATMENT OF DRY EYE

This application is a 371 of PCT/US99/29733 filed on Dec. 14, 1999, which claims the benefits of provisional application No. 60/113,574 filed Dec. 24, 1998.

FIELD OF THE INVENTION

The present invention relates to the use of prostaglandin E receptor agonists and partial agonists to stimulate mucin secretion to treat dry eye, keratoconjunctivitis, Sjogren's syndrome and related ocular surface diseases.

BACKGROUND OF THE INVENTION

Dry eye is a common ocular surface disease afflicting millions of people in the U.S. each year, especially the elderly (Schein et. al., *Prevalence of dry eye among the elderly. American J. Ophthalmology,* 124:723–738, (1997)). Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, the common end result is the breakdown of the tear film, which results in dehydration of the exposed outer surface of the eye. (Lemp, *Report of the Nation Eye Institute/Industry Workshop on Clinical Trials in Dry Eyes, The CLAO Journal,* 21(4):221–231 (1995)). Four events have been identified which singly or in combination are believed to result in the dry eye condition: a) decreased tear production or increased tear evaporation; b) decreased conjunctival goblet-cell density; c) increased corneal desquamation; and d) destabilization of the cornea-tear interface (Gilbard, *Dry eye: pharmacological approaches, effects, and progress. The CLAO Journal,* 22:141–145 (1996)). Another major problem is the decreased mucin production by the conjunctival cells and/or corneal epithelial cells of mucin, which protects and lubricates the ocular surface (Gipson and Inatomi, *Mucin genes expressed by ocular surface epithelium Progress in Retinal and Eye Research,* 16:81–98 (1997)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et. al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et. al.) and U.S. Pat. No. 5,294,607 (Glonek et. al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate tear film; and U.S. Pat. No. 4,966,773 (Gressel et. al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjuctival epithelium of human eyes (Greiner et. al., *Mucus Secretory Vesicles in Conjunctival Epithelial Cells of Wearers of Contact Lenses, Archives of Ophthalmology,* 98:1843–1846 (1980); and Dilly et. al., *Surface Changes in the Anaesthetic Conjunctiva in Man, with Special Reference to the Production of Mucus from a Non-Goblet-Cell Source, British Journal of Ophthalmology,* 65:833–842 (1981)). A number of human-derived mucins which reside in the apical and subapical corneal epithelium have been discovered and cloned (Watanabe et. al., *Human Corneal and Conjuctival Epithelia Produce a Mucin-Like Glycoprotein for the Apical Surface, Investigative Ophthalmology and Visual Science (IOVS),* 36(2):337–344 (1995)). Recently, a new mucin was reported to be secreted via the cornea apical and subapical cells as well as the conjunctival epithelium of the human eye (Watanabe et. al., *IOVS,* 36(2):337–344 (1995)). These mucins provide lubrication, and additionally attract and hold moisture and sebacious material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et. al., *Effect of Intravenously Administered Lipoxygenase Metabolites on Rat Trachael Mucous Gel Layer Thickness, International Archives of Allergy And Applied Immunology*, 90:307–309 (1989)).

The conventional treatment for dry eye, as discussed above, includes administration of artificial tears to the eye several times a day. Other agents claimed for increasing ocular mucin and/or tear production include vasoactive intestinal polypeptide (Dartt et. al., *Vasoactive intestinal peptide-stimulated glycocongjugate secretion from conjunctival goblet cells. Experimental Eye Research*, 63:27–34, (1996)), gefarnate (Nakmura et. al., *Gefarnate stimulates secretion of mucin-like glycoproteins by corneal epithelium in vitro and protects corneal epithelium from dessication in vivo, Experimental Eye Research*, 65:569–574 (1997)), and the use of liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), retinoids (U.S. Pat. No. 5,455,265) and hydroxyeicosatetraenoic acid derivatives (U.S. Pat. No. 5,696,166). However, many of these compounds or treatments suffer from a lack of specificity, efficacy and potency and none of these agents have been marketed so far as therapeutically useful products to treat dry eye and related ocular surface diseases. Thus, there remains a need for an efficacious therapy for the treatment of dry eye and related diseases.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (U.S. Pat. No. 5,151,444; EP 0 561 073 A1; Coleman et. al., *VIII International Union of Pharmacology classification of prostanoid receptors: Properties, distribution, and structure of the receptors and their subtypes, Pharmacological Reviews*, 45:205–229 (1994)). Depending on the number of double-bonds in the α-(top chain) and/or the ω-chain (bottom chain), the prostaglandins are further classified with subscripts such as $PGD_2$, $PGE_1$, $PGE_2$, $PGF_{2\alpha}$, etc. (U.S. Pat. No. 5,151,444; Coleman et. al., *VIII International Union of Pharmacology classification of prostanoid receptors: Properties, distribution, and structure of the receptors and their subtypes, Pharmacological Reviews*, 45:205–229 (1994)). Whilst these classes of prostaglandins interact preferably with the designated major classes of receptors (e.g. DP, EP, FP) and subclasses of receptors (e.g. $EP_2$, $EP_3$, $EP_4$), the subscripts associated with the prostaglandin does not necessarily correspond with the subclass of the receptor(s) with which they interact. Furthermore, it is well known that these endogenous prostaglandins are non-specific in terms of interacting with the various classes of prostaglandin receptors. Thus, $PGE_2$ not only interacts with $EP_2$ receptors, but can also activate $EP_1$, $EP_2$, $EP_3$ and $EP_4$ receptors (Coleman et. al., *VIII International Union of Pharmacology classification of prostanoid receptors: Properties, distribution, and structure of the receptors and their subtypes, Pharmacological Reviews*, 45:205–229 (1994)).

In gastric mucosa, various prostaglandins known to be agonists at one or more of the prostaglandin E receptors have been shown to stimulate mucin secretion (Waterbury et. al., *Stimulation of mucus production and prevention of aspirin induced ulcerogenesis by enprostil in the rat. Proc. West. Pharmacol. Soc.*, 31:21–3 (1988); Enss et. al., *Effects of $PGE_2$ and of different synthetic PGE derivatives on the glycosylation of pig gastric mucins. Prostaglandins, Leukotrienes, Essent. Fatty Acids*, 59:49–54 (1998); Guslandi et. al., *Gastric effects of a prostaglandin E1-derivative (Rioprostil) on acid, alkaline, and mucus secretion. Clin. Ther.*, 8:619–23. Katz et. al., *Antigastrolesive, gastric antisecretory, diarrheagenic, and mucus-stimulating effects in rats following topically applied rioprostil, a synthetic prostaglandin E1 analog. Life Sci.*, 41:1591–8 (1987); Waterbury et. al., *Stimulatory effect of enprostil, an anti-ulcer prostaglandin, on gastric mucus secretion. Am. J. Med.*, 81:30–3 (1986); Perkins et. al., *Antisecretory, mucosal-protective, and diarrheagenic activity of a novel synthetic prostaglandin, SC-46275, in the rat. Drug Dev. Res.*, 23:349–58 (1991); Bunce et. al., *GR63799X—a novel prostanoid with selectivity for $EP_3$ receptors. Adv. Prostaglandin. Thromboxane, Leukotriene Res.* 21A:379–82 (1990); Sellers et. al., *Misoprostol-induced increases in adherent gastric mucus thickness and luminal mucus output. Dig. Dis. Sci.*, 31:91S–95S (1986); Wilson et. al., *Effects of misoprostol on gastric acid and mucus secretion in man. Dig. Dis. Sci.*, 31:126S–129S (1986)). Of interest in the present invention are prostaglandins which are believed to exhibit mucin-producing activity by binding to and activating any of the four recognized prostaglandin E receptors.

SUMMARY OF THE INVENTION

The present invention is directed to compositions and methods for the treatment of dry eye and other disorders requiring the wetting of the eye. More specifically, the present invention discloses compositions containing prostaglandin E receptor agonists and methods for treating dry eye type disorders.

Preferred compositions include an effective amount of a prostaglandin E receptor agonist for the production of mucins in mammals, and especially in humans. The compositions are administered topically to the eye for the treatment of dry eye.

DETAILED DESCRIPTION OF THE INVENTION

It has now been discovered that certain prostaglandin E receptor agonists stimulate mucin production in human conjuctival epithelium and are therefore believed to be useful in treating dry eye. As used herein, the term "prostaglandin E receptor agonist" refers to any compound which acts as an agonist or partial agonist at one of the prostaglandin EP receptors ($EP_1$, $EP_2$, $EP_3$, or $EP_4$), thereby stimulating mucin production and/or secretion in the conjunctival epithelium and goblet cells following topical ocular application. Specifically included in such definition are compounds of the following formula I:

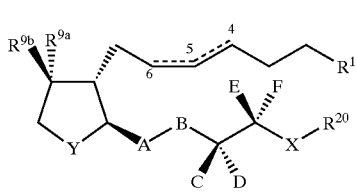

wherein:
$R^1 = (CH_2)_n CO_2 R$, $(CH_2)_n CONR^4 R^5$, $(CH_2)_n CH_2 OR^6$, $(CH_2)_n CH_2 NR^7 R^8$, where:
R=H or pharmaceutically acceptable cationic salt moiety, or $CO_2R$ forms a pharmaceutically acceptable ester moiety;

$R^4$, $R^5$=same or different=H, alkyl, or $SO_2CH_3$, with the proviso that if one of
$R^4$, $R^5$=$SO_2CH_3$, then the other=H or alkyl;
$R^6$=H, acyl, or alkyl;
$R^7$, $R^8$=same or different=H, acyl, or alkyl; with the proviso that if one of
$R^7$, $R^8$=acyl, then the other=H or alkyl;
n=0 or 2;
----=single or double bond, which can be cumulated (i.e., carbons 4–6 can form an allene);
$R^{9b}$=Cl, and $R^{9a}$=H, or $R^{9b}R^{9a}$ taken together=O as a carbonyl;
Y=$CH_2$, O, or

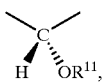

where
$R^{11}$=H, alkyl, or acyl;
A=O and B=$CH_2$; or, A—B=$CH_2CH_2$ or cis-CH=CH; with the proviso that A≠O when Y=O.
one of C, D=H, and the other=$CH_3$ or $OR^2$, where $R^2$=H, acyl, or alkyl; or C=D=H;
E and F=same or different=H or $CH_3$; or one of E, F=$CH_3$ and the other=$OR^2$, where $R^2$ is defined as above; with the proviso that exactly one of C, D, E, and F=$OR^2$;
X=O or direct bond;
$R^{20}$=$C_{2-8}$ alkyl, $C_{2-8}$ alkenyl, aryl, heteroaryl, aryloxy, or heteroaryloxy, optionally substituted with halo, trihalomethyl, $OR^3$, $NR^3R^{21}$, wherein $R^3$=H, alkyl, or acyl; and $R^{21}$=H, alkyl, or acyl; with the proviso that if one of $R^3$ and $R^{21}$=acyl, then the other=H or alkyl: and wherein the $C_{2-8}$ alkyl and $C_{2-8}$ alkenyl may be optionally terminated by $C_{3-8}$ cycloalkyl, $C_{4-8}$ cycloalkenyl, aryl, heteroaryl, aryloxy, or heteroaryloxy, optionally substituted as described above; with the proviso that $R^{20}$≠aryloxy or heteroaryloxy when X=O;
with the proviso that the following compounds of formula I be excluded:
those wherein all of the following limitations are satisfied:
----=a single bond between carbons 4 and 5 and a single or double bond between carbons 5 and 6;
$R^{9a}R^{9b}$=O as a carbonyl;
Y=$CH_2$ or

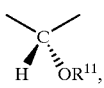

where
$R^{11}$ as defined above;
A—B=$CH_2CH_2$ or CH=CH;
one of C, D=H and the other=$OR^2$, where $R^2$ is as defined above; and
E and F=same or different=H or $CH_3$.

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions.* volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers of the disclosed compounds substantially free of their respective enantiomers.

As used herein, the terms "pharmaceutically acceptable ester"/"pharmaceutically acceptable cationic salt" means any ester/cationic salt that would be suitable for therapeutic administration to a patient by any conventional means without significant deleterious health consequences; and "ophthalmically acceptable ester"/"ophthalmically acceptable cationic salt" means any pharmaceutically acceptable ester/cationic salt that would be suitable for ophthalmic application, i.e. non-toxic and non-irritating. Wavy line attachments indicate that the configuration may be either alpha (α) or beta (β). The carbon numbering is as indicated in formula I, even when n=2. Dashed lines on bonds [e.g., between carbons 4 (C-4) and 5 (C-5)] indicate a single or double bond. Two solid lines present specify the configuration of the relevant double bond. Hatched lines indicate the α configuration. A solid triangular line indicates the β configuration The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred for purposes of the present invention are those compounds of formula I wherein:

$R^1$=$(CH_2)_nCO_2R$ or $(CH_2)_nCH_2OH$, where R=H, ophthalmically acceptable cationic salt moiety, or lower alkyl; and n=0;

----=single or double bond, which can be cumulated (i.e., carbons 4–6 can form an allene);

$R^{9b}$=Cl, and $R^{9a}$=H; or $R^{9b}R^{9a}$ taken together=O as a carbonyl;

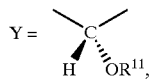

where
$R^{11}$=H;
A—B=cis-CH=CH;
C=D=H;
one of E, F=$CH_3$ and the other=$OR^2$;
$R^2$=H;
X=direct bond; and
$R^{20}$=$C_{2-5}$ alkyl or $C_{2-5}$ alkenyl, where either is optionally terminated by $C_{5-6}$ cycloalkyl or $C_{5-6}$ cycloalkenyl.

Also preferred for purposes of the present invention are those compounds of formula I, wherein:

$R^1$=$(CH_2)_nCO_2R$ or $(CH_2)_nCH_2OH$, where R=H, ophthalmically acceptable cationic salt moiety, or lower alkyl; and n=0;

----=single or double bond, which can be cumulated (i.e., carbons 4–6 can form an allene);

$R^{9b}$=Cl, and $R^{9a}$=H;

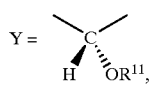

where
$R^{11}$=H;
A—B=cis-CH=CH;
one of C=D=H, and the other=OH;
E=F=$CH_3$;
X=direct bond; and
$R^{20}$=$C_{2-5}$ alkyl or $C_{2-5}$ alkenyl, where either is optionally terminated by $C_{5-6}$ cycloalkyl or $C_{5-6}$ cycloalkenyl.

Also preferred for purposes of the present invention are those compounds of formula I, wherein:

$R^1$=$(CH_2)_nCO_2R$ or $(CH_2)_nCH_2OH$, where R=H, ophthalmically acceptable cationic salt moiety, or lower alkyl; and n=0;

-----=a double bond between carbons 4 and 5 and a single or double bond between carbons 5 and 6;

$R^{9a}R^{9b}$ taken together=O as a carbonyl;

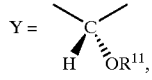

where
$R^{11}$=H
A—B=cis-CH=CH;
one of C=D=H, and the other=OH;
E=F=H;
X=O;
$R^{20}$=phenyl, optionally substituted with Cl or $CF_3$.

Most preferred of the foregoing compounds are the following:

| Compound Name | Compound Structure | Source Reference* |
| --- | --- | --- |
| enprostil | 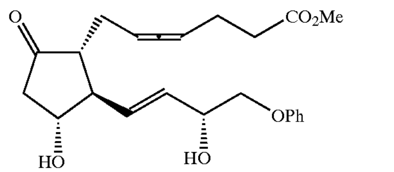 | Cooper et al., J. Org. Chem., 58:4280–4286 (1993); Park et. al., U.S. Pat. No. 5,571,936. |
| rioprostil | 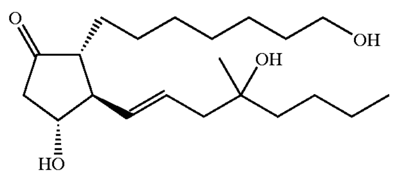 | Shriver et al., EP 66475 A2; Kluender et. al., U.S. Pat. No. 4,132,738 |
| SC-46275 | 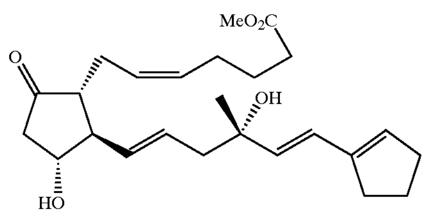 | Kalish et. al., Synth. Commun., 20:1641–5 (1990); Collins et. al., J. Med. Chem., 33:2784–93 (1990); Babiak et. al., U.S. Pat. No. 5,055,604. |
| enisoprost | 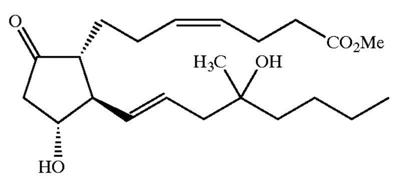 | Babiak et. al., U.S. Pat. No. 5,055,604; Dygos et. al., J. Org. Chem., 56:2549–52 (1990). |
| nocloprost | 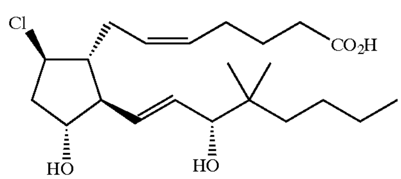 | Skuballa et. al., U.S. Pat. No, 4,444,788. |
| misoprostol | 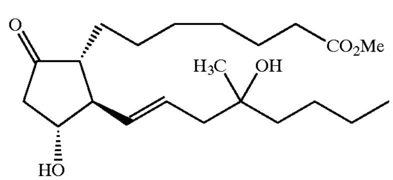 | Commercially available from Cayman Chemical Co., Ann Arbor, MI |

*To the extent the cited references disclose methods of synthesis for the identified compounds, those references are hereby incorporated herein.

The prostaglandin E agonists of the present invention may be contained in various types of pharmaceutical compositions, in accordance with formulation techniques known to those skilled in the art. In general, these compounds will be formulated in solutions for topical ophthalmic administration. Solutions, suspensions and other dosage forms are particularly preferred for the treatment of dry eye.

The ophthalmic compositions of the present invention will include one or more compounds of the present invention in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels, or other types of solid or semi-solid compositions. Suspensions may be preferred for those compounds of the present invention which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the $EP_4$ agonists from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one prostaglandin E agonist of the present invention.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for the treatment of dry eye in mammals comprising administering to an affected eye, a pharmaceutically effective amount of a compound of formula I:

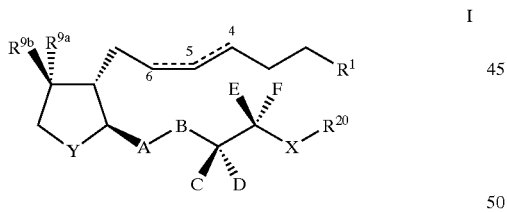

wherein:
$R^1 = (CH_2)_n CO_2 R$, $(CH_2)_n CONR^4 R^5$, $(CH_2)_n CH_2 OR^6$, $(CH_2)_n CH_2 NR^7 R^8$, where:
  R=H or pharmaceutically acceptable cationic salt moiety, or $CO_2R$ forms a pharmaceutically acceptable ester moiety;
  $R^4$, $R^5$=same or different=H, alkyl, or $SO_2CH_3$, with the proviso that if one of $R^4$, $R^5 = SO_2CH_3$, then the other=H or alkyl;
  $R^6$=H, acyl, or alkyl;
  $R^7$, $R^8$=same or different=H, acyl, or alkyl; with the proviso that if one of
  $R^7$, $R^8$=acyl, then the other=H or alkyl;
n=0 or 2;
----=single or double bond, which may be cumulated to form an allene;

$R^{9b}$=Cl, and $R^{9a}$=H, or $R^{9b}R^{9a}$ taken together=O as a carbonyl;
$Y=CH_2$, O, or

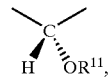

where
$R^{11}$=H, alkyl, or acyl;
$A=O$ and $B=CH_2$; or, $A-B=CH_2CH_2$ or cis-$CH=CH$; with the proviso that $A \neq O$ when $Y=O$.
one of C, D=H, and the other=$CH_3$ or $OR^2$, where $R^2$=H, acyl, or alkyl; or C=D=H;
E and F=same or different=H or $CH_3$; or one of E, F=$CH_3$ and the other=$OR^2$, where
$R^2$ is defined as above; with the proviso that exactly one of C, D, E, and F=$OR^2$;
X=O or direct bond;
$R^{20}$=$C_{2-8}$ alkyl, $C_{2-8}$ alkenyl, aryl, heteroaryl, aryloxy, or heteroaryloxy, optionally substituted with halo, trihalomethyl, $OR^3$, $NR^3R^{21}$, wherein $R^3$=H, alkyl, or acyl; and $R^{21}$=H, alkyl, or acyl; with the proviso that if one of $R^3$ and $R^{21}$=acyl, then the other=H or alkyl; and wherein the $C_{2-8}$ alkyl and $C_{2-8}$ alkenyl may be optionally terminated by $C_{3-8}$ cycloalkyl, $C_{4-8}$ cycloalkenyl, aryl, heteroaryl, aryloxy, or heteroaryloxy, optionally substituted as described above; with the proviso that $R^{20} \neq$ aryloxy or heteroaryloxy when X=O;
with the proviso that the following compounds of formula I be excluded:
  those wherein all of the following limitations are satisfied:
----=a single bond between carbons 4 and 5 and a single or double bond between carbons 5 and 6;
$R^{9a}R^{9b}$=O as a carbonyl;
$Y=CH_2$ or

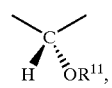

where
$R^{11}$ as defined above;
$A-B=CH_2CH_2$ or $CH=CH$;
one of C, D=H and the other=$OR^2$, where $R^2$ is as defined above; and
E and F=same or different=H or $CH_3$.

2. The method of claim 1, wherein the mammal is a human and the compound is administered topically.

3. The method of claim 2, wherein for the compound of formula I:
$R^1 = (CH_2)_n CO_2 R$ or $(CH_2)_n CH_2 OH$, where R=H, ophthalmically acceptable cationic salt moiety, or lower alkyl; and n=0;
----=single or double bond, which may be cumulated to form an allene;
$R^{9b}$=Cl, and $R^{9a}$=H; or $R^{9b}R^{9a}$ taken together=O as a carbonyl;

Y = 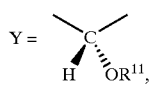

where
$R^{11}$=H;
A—B=cis-CH=CH;
C=D=H;
one of E, F=CH$_3$ and the other=OR$^2$, where $R^2$=H;
X=direct bond; and
$R^{20}$=C$_{2-5}$ alkyl or C$_{2-5}$ alkenyl, where either is optionally terminated by C$_{5-6}$ cycloalkyl or C$_{5-6}$ cycloalkenyl.

4. The method of claim 3, wherein the compound is selected from the group consisting of: rioprostil, SC 46275, enisoprost, and misoprostol.

5. The method of claim 2, wherein for the compound of formula I:
$R^1$=(CH$_2$)$_n$CO$_2$R or (CH$_2$)$_n$CH$_2$OH, where R=H, ophthalmically acceptable cationic salt moiety, or lower alkyl; and n=0;
----=single or double bond, which may be cumulated to form an allene;
$R^{9b}$=Cl, and $R^{9a}$=H;

Y = 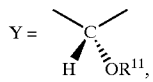

where
$R^{11}$=H;
A—B=cis-CH=CH;
one of C=D=H, and the other=OH;
E=F=CH$_3$;
X=direct bond; and
$R^{20}$=C$_{2-5}$ alkyl or C$_{2-5}$ alkenyl, where either is optionally terminated by C$_{5-6}$ cycloalkyl or C$_{5-6}$ cycloalkenyl.

6. The method of claim 5, wherein the compound is nocloprost.

7. The method of claim 2, wherein for the compound of formula I:
$R^1$=(CH$_2$)$_n$CO$_2$R or (CH$_2$)$_n$CH$_2$OH, where R=H, ophthalmically acceptable cationic salt moiety, or lower alkyl; and n=0;
----=a double bond between carbons 4 and 5 and a single or double bond between carbons 5 and 6;
$R^{9a}R^{9b}$ taken together=O as a carbonyl;

Y = 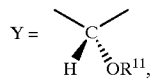

where
$R^{11}$=H;
A—B=cis-CH=CH;
one of C=D=H, and the other=OH;
E=F=H;
X=O;
$R^{20}$=phenyl, optionally substituted with Cl or CF$_3$.

8. The method of claim 7, wherein the compound is enprostil.

* * * * *